United States Patent [19]
Larkin et al.

[11] Patent Number: 5,189,233
[45] Date of Patent: Feb. 23, 1993

[54] PROCESS FOR THE PRODUCTION OF CYCLOHEXANE BY LIQUID PHASE HYDROGENATION OF BENZENE

[75] Inventors: John M. Larkin; James H. Templeton, both of Austin; Donald H. Champion, Pflugerville, all of Tex.

[73] Assignee: Texaco Chemical Company, White Plains, N.Y.

[21] Appl. No.: 749,346

[22] Filed: Aug. 23, 1991

[51] Int. Cl.$^5$ .............................................. C07C 5/00
[52] U.S. Cl. .................................. 585/265; 585/250; 585/266; 585/269; 585/270; 585/277
[58] Field of Search ............... 585/269, 270, 250, 265, 585/266, 277

[56] References Cited

U.S. PATENT DOCUMENTS 3,152,998 10/1964 Moss .................................... 502/315
3,796,764 4/1974 Suggitt et al. ........................ 585/264
3,798,279 3/1974 Cessou et al. ........................ 585/270

Primary Examiner—Patrick P. Garvin
Assistant Examiner—Brent M. Peebles
Attorney, Agent, or Firm—Jack H. Park; Kenneth R. Priem; Cynthia L. Kendrick

[57] ABSTRACT

Disclosed is an improvement in a process for production of cyclohexane by liquid phase hydrogenation of benzene wherein no diluent is necessary, which comprises contacting benzene and hydrogen in the presence of a mixed catalyst bed comprising a first catalyst which is a less active hydrogenation catalyst selected from elements of Group VIII of the Periodic Table and a second, more active catalyst, comprising a Group VIII metal supported on an oxide, such as, for example, alumina, silica or titania at a temperature of about 40° C. to about 300° C. and pressure sufficient to keep the benzene liquid at the chosen reaction temperature.

1 Claim, No Drawings

PROCESS FOR THE PRODUCTION OF CYCLOHEXANE BY LIQUID PHASE HYDROGENATION OF BENZENE

FIELD OF THE INVENTION

The present invention relates to the production of cyclohexane. More particularly this invention relates to an improved process for the production of cyclohexane from benzene in liquid phase which requires no cyclohexane diluent to control the exothermic reaction, avoids the formation of byproducts such as methylcylopentane and requires no separation. This improved process is accomplished by reacting benzene over a mixed catalyst comprising a less active Group VIII catalyst followed by a more active supported Group VIII Catalyst at a temperature of from about 40° C. to about 300° C. and a pressure of atmospheric pressure to about 4000 psig.

BACKGROUND OF THE INVENTION

The hydrogenation of aromatic compounds is well known and has been disclosed throughout the art. In earlier processes when, for example, benzene was contacted with hydrogen in the presence of a hydrogenation catalyst at elevated temperatures and pressures there was typically good conversion of benzene to cyclohexane, however side reactions took place, such as cracking with the production of normal hexane and isomerization with the production of methyl cyclopentane. And, in the case of excessively high temperatures, the formation of C$_5$ and lighter hydrocarbons was observed.

Where cyclohexane is used as an intermediate for the production of other chemicals, it is desirable to obtain the cyclohexane in as high purity as possible. It has been found that in order to do this the reaction temperature must be kept below a threshold where isomerization and cracking occur to a significant extent. In addition, complete hydrogenation is favored thermodynamically by a lower reaction temperature. For example, if the concentration of benzene is to be less than 100 ppm, the reaction must be conducted at less than 235° C. according to thermodynamic calculations.

Hydrogenation is inherently exothermic, so a number of devices have been used to maintain a lower temperature. These include multiple catalyst beds with interbed heat exchange and cooling of the reactant stream and tubular reactors. A preferred process involved introduction of a mixture of benzene feed and cyclohexane product into the multiple catalyst bed unit with the introduction of product cyclohexane between the beds for the purpose of cooling the reactant stream. This effectively resulted in a low space velocity since only a small volume of material being passed through the bed was actually being hydrogenated.

SRI Report No. 713 Supplement B, January 1976, provides a review of a number of processes for hydrogenating benzene, along with important considerations involved in designing systems to accomplish hydrogenation.

In U.S. Pat. No. 3,202,723 there is described a process in which liquid phase is employed in the first reactor and vapor phase in the finishing reactor, where the catalyst in the first reactor comprises suspended Raney nickel.

U.S. Pat. No. 3,070,640, to Kellog, discloses a system wherein the main reactor is a tubular reactor filled with catalysts of progressive activities along the feed passage. The catalysts include nickel, platinum and such on alumina, silica and similar elements. No gain or loss of heat is allowed to occur in the finishing reactor.

A shaft reactor which has catalyst layers of progressively rising activities in the main reactor section is disclosed in British Pat. 1,008,666. Heat is removed by circulating fluid outside the shafts.

A two catalyst scheme is described in British Patent 1,104,275 where the benzene is first contacted with a platinum catalyst followed by a nickel catalyst. The process appears to take place in vapor phase.

In U.S. Pat. No. 3,767,719, to Texaco, there is disclosed a vapor phase tubular reactor containing nickel, platinum and palladium catalysts. The reactor is cooled with a mixture of cyclohexane and feed. The heated medium is flashed and separated into vapor and liquid. The vapor is charged to the catalyst zone while the liquid recirculates to cool.

A two stage reactor is disclosed in U.S. Pat. No. 3,796,764, assigned to Texaco Inc. The first stage comprises nickel on alumina and the second stage comprises platinum on alumina. That process required a cyclohexane diluent for the benzene feed to control the exothermic reaction. The first catalyst is less active than the second which helps to control the heat generated. Moderation of the catalyst activity was accomplished by using a lower metal concentration on the catalyst. The benzene/hydrogen molar ratio was 4:1 to 15:1, the temperature range was 350° F.–680° F. and the pressure was about 300 psig to about 600 psig.

It would be a distinct advance in the art if a process were available which required no diluent circulating in order to control the exothermic reaction. Additional improvements would include improved selectivity for cyclohexane and reduced formation of the by-product methylcyclopentane. A process where the benzene feed remained in liquid phase, along with other hydrocarbons in the process, and where no separation is required would definitely have commercial advantages.

SUMMARY OF THE INVENTION

In the instant invention a process is disclosed which makes these and other desirable objectives possible. A process is disclosed for the liquid phase hydrogenation of benzene which comprises contacting the benzene with a first catalyst bed consisting of a Group VIII metal, optionally mixed with other metals and a second catalyst bed consisting essentially of a Group VIII metal supported on an oxide from the group consisting of alumina, silica and titania, optionally admixed with other metals or metal oxides at a temperature of from about 40° C. to about 300° C. at a pressure from about 500–4000 psig, wherein no cyclohexane diluent is necessary.

Improvements include the lack of necessity for a diluent and a more complete reaction of benzene, resulting in improved selectivity.

DETAILED DESCRIPTION OF THE PREFERRED EMBODIMENT

According to the instant invention, a more complete reaction is achieved by contacting benzene and hydrogen with a less active catalyst followed by contact with a more active catalyst to produce improved yields of cyclohexane. The product cyclohexane is useful in the production of adipic acid.

The first, less active, catalyst comprises a Group VIII metal, optionally mixed with other metals. Suitable Group VIII metals include copper, ruthenium, osmium, cobalt, rhodium, iridium, nickel, palladium and platinum. A metal which functions well is nickel. A preferred nickel catalyst is characterized by having the composition, calculated in mole %, of from about 60–85% nickel, 14–37% copper and 1–6% chromium with the preferred proportions being about 72–78% nickel, 20–25% copper and 1–3% chromium. A particularly preferred hydrogenation catalyst is one in which the active components consist essentially of about 75 mole % nickel, about 23 mole % copper and about 2 mole % chromium in the form of an oxide.

It has been discovered in the instant invention that an effective catalyst in combination with the bulk nickel catalyst is an oxide supported Group VIII metal catalyst. Said oxide supports may be selected from the oxides of Groups IIIA, IVA or IVB of the Periodic Table. The preferred supports include magnesia, alumina, silica, zirconia and titania, as well as mixtures thereof. The preferred support is alumina.

The Group VIII metal can be any of those mentioned above and is preferably nickel, however, the second catalyst should be in a more active form than the first. For example the nickel can be loaded on a support. The nickel may be added to said support by any of the usual methods and said formulated catalyst may comprise from 10 to 80 wt % nickel. The preferred nickel loading is 40 to 60 wt % nickel-on-alumina.

Said combination of catalysts may be used in any proportion as long as the less active catalyst, such as, for example, nickel-copper-chromium, contacts the benzene feed first. The benzene should contact the oxide supported catalyst in order to achieve highest selectivity for cyclohexane.

A particularly effective ratio of nickel-copper-chromium oxide catalyst to oxide-supported nickel catalyst is in the range of 1:10 to 10:1 by volume. The accompanying examples illustrate such a ratio range. A particularly preferred combination is a nickel-copper-chromium oxide catalyst in conjunction with a nickel on alumina catalyst.

The space velocity of the benzene and hydrogen feed may vary depending on reactor design, catalyst, etc. An excess of hydrogen is usually desired to ensure complete hydrogenation. The examples demonstrate a preferred space velocity of about 1.7 g/cc cat/hour benzene and 2.2 l/cc cat/hour hydrogen.

The hydrogen used in the process of this invention should be substantially pure. For this reason it is advantageous to purify the hydrogen by cryogenic means to remove substantially all impurities. This is particularly true when the hydrogen is obtained as by-product from a catalytic reforming unit. Cryogenic purification will then result in the removal of even small amounts of hydrogen sulfide, ammonia and water. Hydrogen purity is not critical but in commercial plants where the hydrogen is recycled, and inerts such as methane can build up, the hydrogen purity should be at least 95%, and preferably at least 99%.

The temperature range for the invention is from 40° C. to about 300° C. The preferred temperature is from about 75° C. to 230° C.

The pressure must be sufficient to keep the benzene liquid at the chosen reaction temperature. A useful range is from about 500 psig to 4000 psig and a preferred pressure is about 1500 psig to about 2500 psig.

The following examples are submitted for illustrative purposes only and are not intended to limit the invention in any way. It is noted that Examples 1 and 2 are comparative in that each contains only the first catalyst alone or the second catalyst alone. Example 3 demonstrates the mixed bed of the invention. The improved yields achieved using the mixed catalyst bed are apparent by reviewing the data for Example 3 in comparison with 1 and 2.

EXAMPLE 1

A 550 cc jacketed stainless steel tubular reactor was charged with 47.5% Ni on alumina 1/16" extrudates. Nitrogen was passed over the catalyst bed at atmospheric pressure as it was heated to 250° C. for 2 hours. The bed was cooled to 200° C. and hydrogen was gradually bled into the reactor. An exotherm was observed in the catalyst bed. The hydrogen concentration was gradually increased to 100%.

Benzene and hydrogen were fed upflow to the reactor at 1.92 lb/h and 1200 l/h (STP), respectively, at 2500 psig and a jacket temperature of 88° C. CG analysis of the effluent showed the product to contain:

| | |
|---|---|
| pentane | 0.073 wt % |
| hexane | 0.063 |
| methylcyclopentane | 0.101 |
| cyclohexane | 99.65 |
| benzene | 0.002 |
| methylcyclohexane | 0.058 |

EXAMPLE 2

Using the reactor described in Example 1, benzene and hydrogen were passed upflow over Ni-Cu-Cr oxide 3/16" (bulk nickel catalyst) at 2.0 lb/h and 1200 l/h (STP) respectively at 2500 psig. Products made at jacket temperatures of 150° C. and 160° C. contained:

| Jacket Temperature (°C.) | 150 | 160 |
|---|---|---|
| hexane | 0.000 wt % | 0.000 |
| methylcyclopentane | 0.006 | 0.006 |
| cyclohexane | 98.96 | 99.69 |
| benzene | 1.03 | 0.298 |
| methylcyclohexane | 0.004 | 0.004 |

EXAMPLE 3

The reactor described in Example 1 was charged with 250 cc Ni-Cu-Cr oxide 3/16" catalyst in the bottom portion and 310 cc 47.5% Ni on alumina 1/16" catalyst on top. Benzene and hydrogen were fed upflow to the reactor at 2.0 lb/h and 1200 l/h (STP), respectively, at 2500 psig and a jacket temperature of 149° C. The product was composed of:

| | |
|---|---|
| pentane | 0.001 wt % |
| hexane | 0.001 |
| methylcyclopentane | 0.005 |
| cyclohexane | 99.99 |
| benzene | 0.001 |
| methylcyclohexane | 0.004 |

What is claimed is:

1. A two-stage, single reactor process for production of cyclohexane by liquid phase hydrogenation of benzene which consisting essentially of using a first catalyst bed consisting essentially of a nickel catalyst having the composition of from 60–85 mol % nickel, 14–37 mol % copper and 1–6 mol % chromium and a second catalyst bed consisting essentially of 10–80 wt % nickel on alumina wherein the temperature range is from about 40° C. to 300° C. and the pressure is from about 500 to 4000 psig.

* * * * *